(12) United States Patent
Fu et al.

(10) Patent No.: US 10,407,455 B2
(45) Date of Patent: Sep. 10, 2019

(54) PHILLYGENIN GLUCURONIC ACID DERIVATIVE AS WELL AS PREPARATION METHOD AND APPLICATION THEREOF

(71) Applicant: Li Fu, Dalian (CN)

(72) Inventors: Li Fu, Dalian (CN); Hongyu Fan, Dalian (CN); Renwu Jiang, Dalian (CN); Yu Zhang, Dalian (CN); Kaiqian Wang, Dalian (CN); Zhengxian Liu, Dalian (CN)

(73) Assignee: Li Fu, Dalian (CN)

( * ) Notice: Subject to any disclaimer, the term of this patent is extended or adjusted under 35 U.S.C. 154(b) by 0 days.

(21) Appl. No.: 15/565,249

(22) PCT Filed: Apr. 7, 2016

(86) PCT No.: PCT/CN2016/078688
§ 371 (c)(1),
(2) Date: Oct. 9, 2017

(87) PCT Pub. No.: WO2016/161951
PCT Pub. Date: Oct. 13, 2016

(65) Prior Publication Data
US 2018/0057523 A1 Mar. 1, 2018

(30) Foreign Application Priority Data
Apr. 8, 2015 (CN) .......................... 2015 1 0164294

(51) Int. Cl.
*A01N 43/04* (2006.01)
*A61K 31/70* (2006.01)
*C07H 15/26* (2006.01)
*C07H 1/08* (2006.01)
*A61P 31/16* (2006.01)
*A61P 29/00* (2006.01)
*A61K 31/7034* (2006.01)
*A61K 31/7028* (2006.01)

(52) U.S. Cl.
CPC .............. *C07H 15/26* (2013.01); *A61P 29/00* (2018.01); *A61P 31/16* (2018.01); *C07H 1/08* (2013.01); *A61K 31/70* (2013.01); *A61K 31/7028* (2013.01); *A61K 31/7034* (2013.01)

(58) Field of Classification Search
None
See application file for complete search history.

(56) References Cited

FOREIGN PATENT DOCUMENTS

CN 104945452 A 9/2015

OTHER PUBLICATIONS

Soler, A. et al., "Digestion stability and evaluation of the metabolism and transport of olive oil phenols in the human small-intestinal epithelial Caco-2/TC7 cell line", Food Chemistry, Dec. 31, 2010, pp. 703-714, vol. 119, No. 2.

Duan, L. et al., "Effect of Phillyrin on Gene Expression of Influenza A Virus Nucleoprotein", Chinese General Practice, Jun. 30, 2012, pp. 2082-2084, vol. 15, No. 6C.
Fan, H. et al., "Synthesis and Structure Characterization of Phillyrin", Liaoning Chemical Industry, Mar. 31, 2014, pp. 241-243, vol. 43, No. 3.
Watanabe et al., "Synthesis of the metabolites of a free radical scavenger edaravone (MCI-186, Radicut)", Redox Report, 2003, pp. 157-161, vol. 8, No. 3.
Tanpure et al., "Regio-and Stereoselective Synthesis of Mono-β-d-Glucuronic Acid Derivatives of Combretastatin A-1", Nat. Prod., 2010, pp. 1-61, vol. 73 (6).
O'Neill et al., "Efficient Preparations of the β-Glucuronides of Dihydroartemisinin and Structural Confirmation of the Human Glucuronide Metabolite", J. Med. Chem., 2001, pp. 1467-1470, vol. 44.
Wang, et al., Resveratrol Glucuronides as the Metabolites of Resveratrol in Humans: Characterization, Synthesis, and Anti-HIV Activity, Journal of Pharmaceutical Sciences, Oct. 2014, pp. 2448-2457, vol. 93, No. 10.
Ye et al., "Determination of phillygenin in rat plasma by high-performance liquid chromatography and its application to pharmacokinetic studies", Eur J Drug Metab Pharmacokinet, 2013, pp. 201-207, vol. 38.

*Primary Examiner* — Patrick T Lewis
(74) *Attorney, Agent, or Firm* — Greer, Burns & Crain, Ltd.

(57) ABSTRACT

The present invention provides a novel phillygenin glucuronic acid derivative shown as a general formula (I).

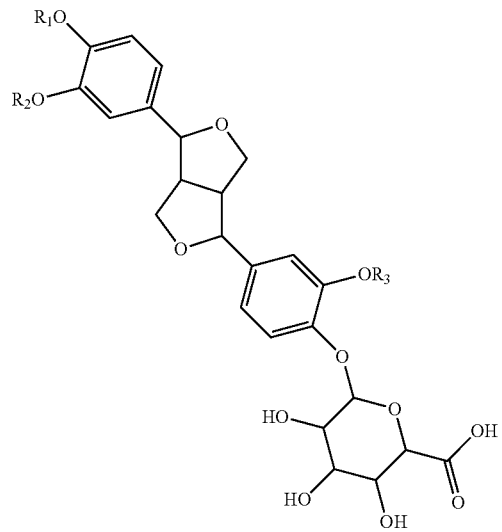

wherein, $R_1$=H, $R_2$=$C_nH_{2n+1}$, $R_3$=$C_nH_{2n+1}$ or $R_1$=$C_nH_{2n+1}$, $R_2$=$C_nH_{2n+1}$, $R_3$=H or $R_1$-$R_2$=—$CH_2$—, $R_3$=$C_nH_{2n+1}$; n=1-30. The present invention further relates to a preparation method of the compound, a pharmaceutical composition taking the compound as an active ingredient, as well as application of the compound in the present invention in antiviral diseases.

7 Claims, No Drawings

PHILLYGENIN GLUCURONIC ACID DERIVATIVE AS WELL AS PREPARATION METHOD AND APPLICATION THEREOF

This application is the U.S. National phase application corresponding to PCT/CN2016/078688 which was assigned an international filing date of Apr. 7, 2016 and associated with publication WO 2016/161951 A1 and which claims priority to Chinese Application 201510164294.6 filed on Apr. 8, 2015, the disclosures of which are expressly incorporated herein by reference.

TECHNICAL FIELD

The present invention belongs to the technical field of drugs, and particularly relates to a preparation method of phillygenin glucuronic acid derivative and antiviral effects of the phillygenin glucuronic acid derivative.

BACKGROUND ART

Phillygenin glucuronide derivatives are active ingredients extracted from dried leaves of Oleaceae *Forsythia suspensa* (Thunb.) vahl. *Forsythia* serving as a traditional Chinese medicine has been applied for a history of two thousand years, and was began to be present in *Shennong's Herbal Classic*. The *Shennong's Herbal Classic* indicated as follows: "the *forsythia* is mainly used for treating chills and fever, carbuncles, malignant sores, stagnation of pathogenic heat, and scrofula." Since Murakami extracted oleanolic acid from *forsythia* fruits first, more than sixty components in the *forsythia* and congeneric plants thereof have been reported. The components mainly contain terpenes, phenethyl alcohol and glycosides thereof, lignans, flavonoids and some alcohol, ester, ether, ketone and other compounds.

Lignan components in the *forsythia* mainly refer to lignanolide and bisepoxylignans. Nishibe et al. extracted arctigenin, mataresinol, arctiin and matairesinoside from the *forsythia* in 1978. Tsukamoto et al. extracted phillygenin, (+)-pinoresinol, phillyrin, (+)-pinoresnol-β-D-glucoside and (+)-epinoresinol-4-O-glucoside from the *forsythia* fruits in 1985. Liu Donglei et al. extracted (+)pinoresinolmonomethylether-β-D-glucoside) from the *forsythia* fruits in 1997. Recent biosynthesis study shows that a lignan precursor in the *forsythia* is coniferyl alcohol. For lignan and glycosides thereof in known *forsythia*, 3,3' totally substituted by methoxy, 4,4' may be hydroxyl, substituted by methoxy or form glycosides with saccharides.

Three phillygenin glucuronide derivatives are first discovered from *forsythia* leaves. Glucuronic acid derivatives have good activities, e.g. artemisinin glucuronic acid derivatives (Efficient Preparations of the β-Glucuronides of Dihydroartemisinin and Structural Confirmation of the Human Glucuronide Metabolite. Paul M. O'Neill, Feodor Scheinmann, Andrew V. Stachulski, James L. Maggs, and B. Kevin Park. J. Med. Chem., 2001, 44(9), pp 1467-1470); edaravone glucuronic acid derivatives (Synthesis of the metabolites of a free radical scavenger edaravone (MCI-186, Radicut™). Kazutoshi Watanabe, Masao Taniguchi, Masaki Shinoda. Redox Report, Vol. 8, No. 3, 2003, 157-161), combretastatin A-1 glucuronic acid derivatives (Regio- and Stereospecific Synthesis of Mono-β-d-Glucuronic Acid Derivatives of Combretastatin A-1.Rajendra P. Tanpure, Tracy E. Strecker, David J. Chaplin, Bronwyn G. Siim, Mary Lynn Trawick and Kevin G. Pinney J. Nat. Prod., 2010, 73(6), pp 1093-1101); resveratrol glucuronic acid derivatives (WANG LAIXI; Heredia, A.; Song, H J; ZHANG ZHAOJUN; Y U BIAO; Davis, C.; Redfield, R. Resveratrol glucuronides as the metabolites of resveratrol in humans: Characterization, synthesis, and anti-HIV activity. J. Pharm. Sci. 2004, 93(10), 2448-2457); curcumin glucuronic acid derivatives (K. S. Psrvathy, M. Sc. University of Mysore. 2009), etc. Therefore, preparation methods of the three phillygenin glucuronide derivatives are researched, and pharmacological study is carried out.

SUMMARY OF THE INVENTION

The present invention aims to provide a novel antiviral drug source, phillygenin glucuronic acid derivatives, preparation methods of the phillygenin glucuronic acid derivatives and application of the phillygenin glucuronic acid derivatives in antiviral. The phillygenin glucuronic acid derivatives provided by the invention have antiviral effects and can be used in preparation of drugs or health care products for treating and preventing influenza viruses. The preparation methods of the phillygenin glucuronic acid derivatives are simple in process, convenient to operate and suitable for large-scale industrial production.

In order to achieve the purpose of the present invention, on one hand, the present invention provides a phillygenin glucuronic acid derivative with a general molecular formula shown as a formula (I):

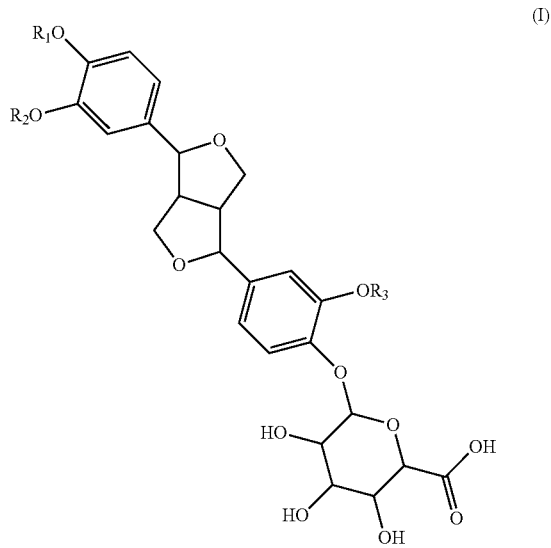

wherein, $R_1=H$, $R_2=C_nH_{2n+1}$, $R_3=C_nH_{2n+1}$ or $R_1=C_nH_{2n+1}$, $R_2=C_nH_{2n+1}$, $R_3=H$ or $R_1-R_2=-CH2-$, $R_3=C_nH_{2n+1}$; $n=1-30$.

wherein, n in the substituent group is equal to 1.

On the other hand, the present invention provides a preparation method of the phillygenin glucuronic acid derivative. The preparation method sequentially comprises the following steps:
1) mixing *forsythia* leaves and extraction solvent water and heating, decocting and extracting for 2-3 times, and collecting and merging the extracting solution so as to obtain a *forsythia* water extract;
2) separating the *forsythia* water extract by adopting a macroporous resin column, and collecting and merging the eluent so as to obtain a *forsythia* resin column eluent;
3) drying the *forsythia* resin column eluent, performing silica-gel column chromatography, collecting the eluent at stages, respectively drying the eluent, thereby obtaining the product.

The heating and extracting frequency in the step 1) is preferably two times. Particularly, in each decocting and extracting process, a weight ratio of the *forsythia* leaves to the extraction solvent water is 1: (6-10), preferablyl: 1: (8-10).

More particularly, in the first decocting process, the weight ratio of the *forsythia* leaves to the extraction solvent water is 1: (9-10); and in the second decocting process, the weight ratio of the *forsythia* leaves to the extraction solvent water is 1:8.

Particularly, the preparation method further comprises the steps: concentrating the *forsythia* water extract obtained in the step 1), preparing a *forsythia* concentrated solution, and performing the macroporous resin column separation treatment.

More particularly, a ratio of the volume of the *forsythia* concentrated solution obtained by concentration to the weight of the *forsythia* leaves is (1-5):1, preferably (2-2.5):1, wherein, the operation of performing macroporous resin column chromatography in the step 2) sequentially comprises the following sub-steps: injecting the *forsythia* water extract into the macroporous resin column, and eluting by taking water as an eluant; eluting by taking an ethanol solution with a mass concentration of 3-50% as an eluant; and finally, eluting by taking absolute ethyl alcohol as an eluant, collecting the absolute ethyl alcohol eluent, thereby obtaining the *forsythia*-macroporous resin eluent.

Particularly, in the macroporous resin column chromatography process, a ratio of the weight of the *forsythia* leaves in the *forsythia* water extract to the volume of the macroporous resin is 1:(0.8-2.5), preferably 1:1.

More particularly, in the macroporous resin column separation process, a ratio of the column diameter of the macroporous resin column to the column height of the resin is 1:5-10, preferably 1:(5-7), further preferably 1:(5.5-5.9), wherein, in the step 2), the macroporous resin is selected from one of X-5, AB-8, NK-2, NKA-2, NK-9, D3520, D101 and WLD, preferably X-5 or AB-8.

Particularly, in the elution process of taking the water as the eluant, a ratio of the usage amount of the water to the column volume of the macroporous resin column is (2-4):1, preferably 4:1; in the elution process of taking the ethanol solution with the mass concentration of 3-50% as the eluant, a ratio of the usage amount of the ethanol solution at the mass concentration of 3-50% to the column volume of the macroporous resin column is (2-8):1, preferably (4-8):1, further preferably 8:1; and in the elution process of taking the absolute ethyl alcohol solution as the eluant, a ratio of the usage amount of the absolute ethyl alcohol solution to the column volume of the macroporous resin column is (2-8):1, preferably (4-8):1, further preferably 8:1, wherein, the operation of performing silica-gel column chromatography in the step 3) sequentially comprises the following sub-steps:
A) concentrating the *forsythia* resin column eluent, and drying so as to obtain crude *forsythia* product;
B) dissolving the crude *forsythia* product in water, injecting the crude *forsythia* product into a silica-gel column, performing silica-gel column chromatography, collecting the eluent at stages, and respectively drying the eluent, thereby obtaining the product.

Particularly, in the step B), the silica-gel column is selected from a reversed-phase silica-gel column, wherein, in the reversed-phase silica-gel column, packing is selected from C18 reversed-phase silica-gel; and a particle size of the silica-gel column is 5-10 μm.

Particularly, the reversed-phase silica-gel column has a column internal diameter of 10-100 mm and a length of 100-300 mm, preferably the column internal diameter of 22.2 mm and the length of 250 mm, wherein, a high performance liquid chromatographic column is selected for performing the silica-gel column chromatography.

Particularly, a mobile phase in the silica-gel column chromatography process is selected from a mixed solution of methanol (A) and water (B), wherein, a volume ratio of the methanol (A) to the water (B) is 8:2-10:1.

Particularly, in the silica-gel column chromatography process, a column temperature is 20-35° C.; and flow velocity is 4-30 ml/min.

Particularly, samples are eluted by the mobile phase in an isocratic elution manner or a gradient elute manner in the silica-gel column chromatography process, wherein, gradient elute refers to [0 min(30% A)→25 min(50% A)→50 min(50% A); the flow velocity is 4.0 mL/min; the column temperature is 20° C.; and a detection wavelength is 273 nm.

Particularly, chromatographic conditions of the silica-gel column chromatography are as follows: the C18 reversed-phase silica-gel serves as a filling agent (Φ22.2×250 mm, 10 μm); methanol (A)-water (B) serves as the mobile phase; gradient elute: 0-25 min, the methanol concentration is 30%-50%; gradient elute: 25-50 min, the methanol concentration is 50%-50%; the flow velocity is 4.0 ml/min; the column temperature is 20° C.; and an UV detection wavelength is 273 nm.

The phillygenin glucuronic acid derivative prepared by the method may be compounds I, II and III.

The structure is confirmed and analyzed as follows:

The compound I: 33-Hydroxy phillygenin-8-O-β-D-glucuronide

ESI-MS: m/z 533.1658 [M-H]$^-$, molecular weight: 534; molecular formula: $C_{26}H_{30}O_{12}$.

Hydrogen nuclear magnetic resonance (400 MHz, $d_6$-DMSO): δ(ppm): 12.0(1H, s, COOH), 7.119-7.099(1H, d, J=8.0 Hz, Ar—H), 6.530-6.943(2H, d, J=4.0 Hz, Ar—H), 6.872(3H, s, Ar—H), 5.39(2H, s, J=4.8 Hz), 5.23(1H, d, J=4.8 Hz), 5.1(1H, d, J=4.8 Hz), 4.800(1H, d, J=4.8 Hz), 4.374-4.388(1H, d, J=9.6 Hz), 4.105-4.085(1H, d, J=8.0 Hz), 4.005-3.982(1H, d, J=9.2 Hz), 3.75(8H, d, J=8.4 Hz), 3.422(1H, t, J=8.7 Hz), 3.08(1H, t, J=8.0 Hz), 2.85(1H, d, J=7.2 Hz);

Carbon nuclear magnetic resonance (100 MHz, $d_6$-DMSO): δ(ppm):172.75 (C-17), 149.51(C-9), 148.95(C-34), 148.09(C-33), 145.74(C-8), 136.26(C-11), 131.67(C-30), 118.55(C-12), 118.05(C-31), 115.72(C-13), 112.03(C-32), 111.07(C-10), 109.92(C-35), 100.21(C-2), 87.11(C-26), 81.74(C-22), 76.26(C-6), 75.70(C-3), 73.41(C-5), 71.91(C-4), 70.81(C-28), 69.46(C-24), 56.15(C-21), 55.99(C-38), 54.47(C-29), 49.79(C-25).

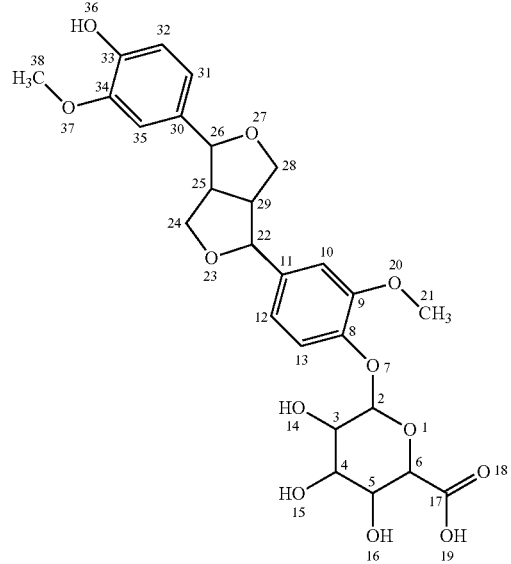 [SMILES: COc1cc(C2OCC3C(c4ccc(OC5OC(C(=O)O)C(O)C(O)C5O)c(OC)c4)OCC23)ccc1O]

The compound II: 9-Hydroxy phillygenin-8-Oβ-D-glucuronide

ESI-MS m/z 533.1641[M-H]⁻, molecular weight: 534; molecular formula: $C_{26}H_{30}O_{12}$.

Hydrogen nuclear magnetic resonance (400 MHz, $d_6$-DMSO): δ(ppm):12.0(1H, s, COOH), 7.119-7.099(1H, d, J=8.0 Hz, Ar—H), 6.530-6.943(2H, d, J=4.0 Hz, Ar—H), 6.872(3H, s, Ar—H), 5.39(2H, s, J=4.8 Hz), 5.23(1H, d, J=4.8 Hz), 5.1(1H, d, J=4.8 Hz), 4.800(1H, d, J=4.8 Hz), 4.374-4.388(1H, d, J=9.6 Hz), 4.105-4.085(1H, d, J=8.0 Hz), 4.005-3.982(1H, d, J=9.2 Hz), 3.75(8H, d, J=8.4 Hz), 3.422(1H, t, J=8.7 Hz), 3.08(1H, t, J=8.1 Hz), 2.85(1H, d, J=7.2 Hz);

Carbon nuclear magnetic resonance (100 MHz, $d_6$-DMSO): δ(ppm):173.72(C-17), 149.51(C-33), 148.95(C-34), 148.09(C-9), 144.74(C-8), 136.26(C-11), 131.67(C-30), 121.45(C-12), 119.72(C-31), 118.05(C-13), 115.07(C-10), 113.03(C-32), 109.92(C-35), 100.21(C-2), 87.11(C-26), 81.74(C-22), 76.26(C-6), 75.70(C-3), 73.41(C-5), 71.91(C-4), 70.81(C-28), 69.46(C-24), 56.15(C-21), 55.99(C-38), 54.47(C-29), 50.16(C-25).

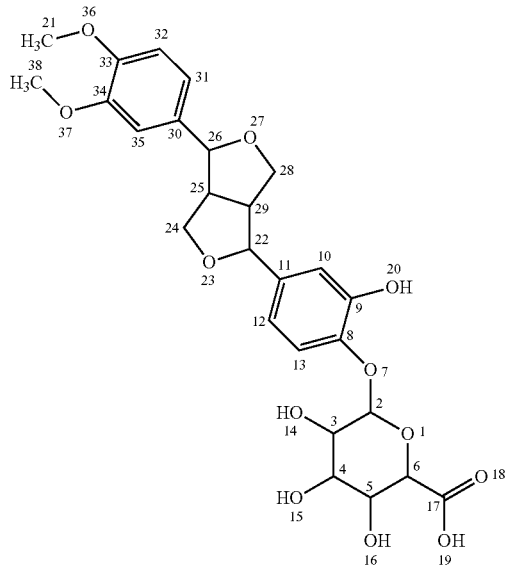 [SMILES: COc1ccc(C2OCC3C(c4ccc(OC5OC(C(=O)O)C(O)C(O)C5O)c(O)c4)OCC23)cc1OC]

The compound III: 33,34-Methylenedioxy phillygenin-8-O-β-D-glucuronide

ESI-MS m/z 531.4933[M-H]⁻, molecular weight: 532; molecular formula: $C_{26}H_{28}O_{12}$.

Hydrogen nuclear magnetic resonance (400 MHz, $d_6$-DMSO): δ(ppm):12.0(1H, s, COOH), 7.119-7.099(1H, d, J=8.0 Hz, Ar—H), 6.530-6.943(2H, d, J=4.0 Hz, Ar—H), 6.872(3H, s, Ar—H), 6.12(2H, s), 5.39(2H, s, J=4.8 Hz), 5.23(1H, d, J=4.8 Hz), 5.1(1H, d, J=4.8 Hz), 4.800(1H, d, J=4.8 Hz), 4.374-4.388(1H, d, J=9.6 Hz), 4.105-4.085(1H, d, J=8.0 Hz), 4.005-3.982(1H, d, J=9.2 Hz), 3.75(8H, d, J=8.4 Hz), 3.422(1H, t, J=8.7 Hz), 3.08(1H, t, J=8.1 Hz), 2.85(1H, d, J=7.2 Hz);

Carbon nuclear magnetic resonance (100 MHz, $d_6$-DMSO): δ(ppm):169.75(C-17), 149.51(C-9), 148.95(C-34), 148.09(C-33), 145.74(C-8), 136.26(C-11), 131.67(C-30), 118.55(C-12), 118.05(C-13), 115.72(C-31), 112.03(C-32), 111.07(C-10), 109.92(C-35), 101.21(C-2), 100.29(C-38), 87.11(C-26), 81.74(C-22), 76.26(C-6), 75.70(C-3), 73.41(C-16), 71.91(C-4), 70.81(C-28), 69.46(C-24), 56.15(C-21), 54.47(C-29), 49.79(C-25).

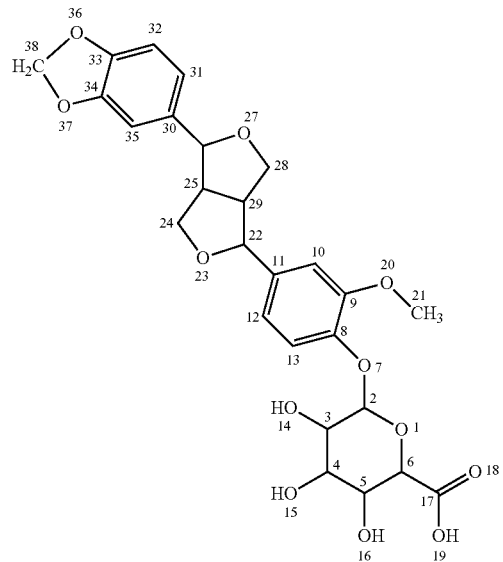 [SMILES: COc1cc(C2OCC3C(c4ccc5c(c4)OCO5)OCC23)ccc1OC1OC(C(=O)O)C(O)C(O)C1O]

According to the method in the present invention, most of the impurities can be removed through purification of the macroporous resin column, and the macroporous resin can be recycled, so that the production cost is reduced, and the service life of a semi-preparative chromatographic column in the next step is prolonged. The process is convenient and easy to operate, high in extraction efficiency and less in pollution, and the prepared product is high in purity and can be industrialized easily.

In another aspect, the present invention provides antiviral application of the phillygenin glucuronic acid derivatives.

In another aspect, the present invention provides purposes of the phillygenin glucuronic acid derivatives in preparation of drugs for preventing or/and treating influenza viruses.

The present invention provides a drug or a health care product composition with an antiviral effect comprising the phillygenin glucuronic acid derivative.

Particularly, the pharmaceutical composition comprises the phillygenin glucuronic acid derivative in the present invention, as well as pharmaceutically acceptable excipients.

The preparation method of the phillygenin glucuronide derivative and the purposes in the drugs for preventing and treating the influenza viruses are not simultaneously limited to the compounds. The phillygenin glucuronide derivative further comprises derivatives prepared by synthesis, fermentation and other methods by taking the compounds as parent nucleuses.

In the present invention, the pharmaceutically acceptable excipients refer to nontoxic solid, semi-solid or liquid filling agents, diluents, carriers, pH regulators, ion intensity regulators, sustained-release or controlled-release preparations, coating materials or other preparation excipients. The used carriers can be matched with corresponding administration forms. The excipients known by those skilled in the art can be prepared into injection, freeze-dried powder (for injection), spray, oral solutions, oral suspension, tablets, capsules, enteric-coated tablets, pills, powder, granules, sustained-release or delayed-release preparations, etc. Preferably, 4-demethylation phillygenin glucuronide in the first aspect of the present invention is administrated through injection or through a digestive tract. Therefore, the pharmaceutical composition in the present invention is preferably injection or a preparation administrated through the digestive tract, that is, preferably the excipients are suitable to be prepared into the preparations administrated through injection or through the digestive tract, wherein "administration through the digestive tract" refers to a manner of administrating the drug preparation through the digestive tract of a patient in the present invention, and comprises oral administration, intragastric administration, clyster administration, etc., preferably the oral administration. For example, the excipients known by those skilled in the art can be prepared into the oral solutions, oral suspension, tablets, capsules, enteric-coated tablets, pills, powder, granules, sustained-release or delayed-release preparations, etc., wherein the preparations administrated through injection mainly refer to injection and powder-injection.

The novel compounds, namely the phillygenin glucuronic acid derivatives, in the present invention have antiviral effects and can be prepared into antiviral, antipyretic, antalgic and anti-inflammatory drugs or health care products. The preparation method of the phillygenin glucuronic acid derivatives is easily controllable in operating process conditions, high in quality controllability, high in yield, low in energy consumption, environment-friendly and suitable for large-scale industrial production.

DETAILED DESCRIPTION OF THE INVENTION

The present invention is further described below through embodiments. However, the embodiments are only for illustrating the present invention, but should not be construed as limiting the scope of the present invention.

Embodiment 1

1. Decocting Treatment 1-1) grinding *forsythia* leaves and enabling the forsythia leaves to pass through a 20-mesh sieve so as to obtain *forsythia* leaf powder, adding 10 kg of water into 1 kg of the *forsythia* leaves, uniformly mixing and heating, and performing the first decocting treatment, wherein a weight ratio of the added water to the *forsythia* leaves is 10:1; and heating and boiling, decocting and extracting for 2 hours, filtering so as to obtain a first extracting solution, and a first drug residue;

1-2) adding 8 kg of water into the first drug residue, heating and boiling, and performing the second decocting treatment, wherein a weight ratio of the added water to the *forsythia* leaves is 8:1; and decocting and extracting for an hour, filtering so as to obtain a second extracting solution, and a drug residue (discarding);

1-3) merging the first extracting solution and the second extracting solution so as to prepare a *forsythia* water extract;

1-4) performing vacuum concentration treatment on the *forsythia* water extract in a vacuum rotary evaporator, and recovering a solvent, thereby obtaining a *forsythia* concentrated solution (2 L) for later use, wherein a ratio of the weight of the *forsythia* leaves to the volume of the *forsythia* concentrated solution is 1:2;

2. Macroporous Resin Column Chromatography 2-1) loading the *forsythia* concentrated solution to a macroporous resin column, and performing macroporous resin column separation treatment, wherein the macroporous resin is selected from an AB-8 type macroporous resin; a column volume of the macroporous resin in the macroporous resin column is 1 L (the chromatographic column has a diameter of 60 mm and a height of 500 mm, and a height of the filled resin is 354 mm); a ratio of the volume of the resin in the resin column to the weight (dry weight) of the *forsythia* leaves is 1:1 (e.g. if the dry weight of the *forsythia* leaves is 1 kg, the volume of the macroporous resin is 1 L; and if dry weight of medicinal materials is1 g, the volume of the macroporous resin is 1 ml); washing with water in an amount of 4 times the volume of the column (that is, 4 L) and removing the eluent after a concentrated supernatant completely flows into the resin column; eluting with an ethanol solution at a mass concentration of 3% in an amount of 8 times the volume of the column (that is, 8 L), and removing the eluent; and eluting with an absolute ethyl alcohol in an amount of 8 times the volume of the column (that is, 8 L), and collecting the eluent, thereby obtaining a *forsythia*-macroporous resin eluent;

2-2) performing vacuum concentration treatment on the *forsythia*-macroporous resin eluent in a rotary evaporator, recovering a solvent, drying the concentrated residue, thereby obtaining 62 g of crude *forsythia* product;

3. Performing Silica-Gel Column Chromatography 3-1) weighing 0.5 g of the crude *forsythia* product, adding a proper amount of water (2.5 ml, and stirring and dissolving for later use;

3-2) performing chromatography treatment on the crude *forsythia* product by adopting a high-performance liquid chromatograph (a Shimadzu SCL-10AVP semi-preparative high-performance liquid chromatograph, an LC-8A pump and an SPD-20A monitor), separating and purifying the crude *forsythia* product, injecting (loading) the dissolved crude *forsythia* product into the semi-preparative high-performance liquid chromatograph, and performing gradient elute by taking a methanol-water solution as an eluent, wherein: a size of a chromatographic column in the high-performance liquid chromatograph is Φ22.2×250 mm, C18 reversed-phase silica-gel serves as packing, the particle size is 10 μm, the loading quantity is 500 mg, the methanol-water solution serves as a mobile phase, conditions of the gradient elute are that: gradient elute: 0-25min, the methanol concentration is 30%-50%; gradient elute: 25-50 min, the methanol concentration is 50%-50%; the flow velocity is 4 ml/min; the column temperature is 20° C.; and an UV detection wavelength is 273 nm; and respectively collecting fractions at retention time of 25.5-27.5 min, 30.5-32.5 min and 35.5-37.5 min;

3-3) respectively performing vacuum concentration on the three collected fractions, performing vacuum drying, thereby obtaining a compound I (70.5 mg), a compound II (53.2 mg) and a compound III (46.6 mg) respectively.

The content of the compounds I, II and III is respectively detected by adopting HPLC (High Performance Liquid Chromatography), and detection conditions of the HPLC comprise: instrument: Water 515 pump; 2487 detector; chromatographic column: Kromasil RP-C18; mobile phase: acetonitrile: 0.1% phosphoric acid solution (13:87); detection wavelength: 230 nm; and flow velocity: 1.0 ml/min.

According to the HPLC detection, the purity of the compound I is 99.6%, the purity of the compound II is 98.1%, and the purity of the compound III is 98.3%.

The compound I is a white solid with a melting point of 111° C. and is soluble in water and ethanol. When expanded on a TLC board (a chromatographic solution of chloroform/methanol 3:1, Rf of 0.25) and sprayed with a 10% $H_2SO_4$-ethanol reagent, the compound I is purplish red.

ESI-MS: m/z 533.1658[M-H]$^-$, molecular weight: 534.

Hydrogen nuclear magnetic resonance (400 MHz, $d_6$-DMSO): δ(ppm):12.0(1H, s, COOH), 7.119-7.099(1H, d, J=8.0 Hz, Ar—H), 6.530-6.943(2H, d, J=4.0 Hz, Ar—H), 6.872(3H, s, Ar—H), 5.39(2H, s, J=4.8 Hz), 5.23(1H, d, J=4.8 Hz), 5.1(1H, d, J=4.8 Hz), 4.800(1H, d, J=4.8 Hz), 4.374-4.388(1H, d, J=9.6 Hz), 4.105-4.085(1H, d, J=8.0 Hz), 4.005-3.982(1H, d, J=9.2 Hz), 3.75(8H, d, J=8.4 Hz), 3.422 (1H, t, J=8.7 Hz), 3.08(1H, t, J=8.1 Hz), 2.85(1H, d, J=7.2 Hz);

Carbon nuclear magnetic resonance (100 MHz, $d_6$-DMSO): δ(ppm):172.75(C-17), 149.51(C-9), 148.95(C-34), 148.09(C-33), 145.74(C-8), 136.26(C-11), 131.67(C-30), 118.55(C-12), 118.05(C-31), 115.72(C-13), 112.03(C-32), 111.07(C-10), 109.92(C-35), 100.21(C-2), 87.11(C-26), 81.74(C-22), 76.26(C-6), 75.70(C-3), 73.41(C-5), 71.91(C-4), 70.81(C-28), 69.46(C-24), 56.15(C-21), 55.99(C-38), 54.47(C-29), 49.79(C-25).

According to test data of ESI-MS, $^1$H-NMR and $^{13}$C-NMR, the compound I is determined to have an English name of 33-Hydroxy phillygenin-8-O-β-D-glucuronide. A structural formula of the compound I is as follows:

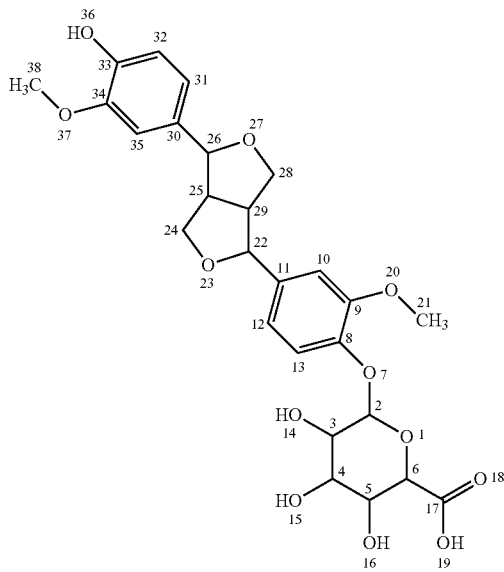 [SMILES: COc1cc(C2OCC3C(c4ccc(OC5OC(C(=O)O)C(O)C(O)C5O)c(OC)c4)OCC23)ccc1O]

The compound II is a white solid with a melting point of 113° C. and is soluble in water and ethanol.

When expanded on the TLC board (a chromatographic solution of chloroform/methanol 3:1, Rf of 0.32) and sprayed with the 10% $H_2SO_4$-ethanol reagent, the compound II is purplish red.

ESI-MS m/z 533.1641 [M-H]$^-$, molecular weight: 534.

Hydrogen nuclear magnetic resonance (400 MHz, $d_6$-DMSO): δ(ppm):12.0(1H, s, COOH), 7.119-7.099(1H, d, J=8.0 Hz, Ar—H), 6.530-6.943(2H, d, J=4.0 Hz, Ar—H), 6.872(3H, s, Ar—H), 5.39(2H, s, J=4.8 Hz), 5.23(1H, d, J=4.8 Hz), 5.1(1H, d, J=4.8 Hz), 4.800(1H, d, J=4.8 Hz), 4.374-4.388(1H, d, J=9.6 Hz), 4.105-4.085(1H, d, J=8.0 Hz), 4.005-3.982(1H, d, J=9.2 Hz), 3.75(8H, d, J=8.4 Hz), 3.422(1H, t, J=8.7 Hz), 3.08(1H, t, J=8.1 Hz), 2.85(1H, d, J=7.2 Hz);

Carbon nuclear magnetic resonance (100 MHz, $d_6$-DMSO): δ(ppm): 173.72(C-17), 149.51(C-33), 148.95 (C-34), 148.09(C-9), 144.74(C-8), 136.26(C-11), 131.67(C-30), 121.45(C-12), 119.72(C-31), 118.05(C-13), 115.07(C-10), 113.03(C-32), 109.92(C-35), 100.21(C-2), 87.11(C-26), 81.74(C-22), 76.26(C-6), 75.70(C-3), 73.41(C-5), 71.91(C-4), 70.81(C-28), 69.46(C-24), 56.15(C-21), 55.99(C-38), 54.47(C-29), 50.16(C-25).

According to test data of ESI-MS, and $^1$H-NMR, and $^{13}$C-NMR, the compound II is determined to have an English name of 9-Hydroxy phillygenin-8-O-β-D-glucuronide.

A structural formula of the compound II is as follows:

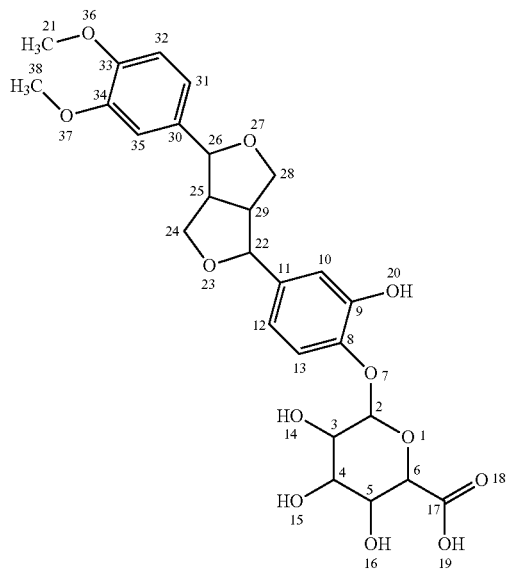 [SMILES: COc1ccc(C2OCC3C(c4ccc(OC5OC(C(=O)O)C(O)C(O)C5O)c(O)c4)OCC23)cc1OC]

The compound III is a white solid with a melting point of 119° C. and is soluble in water and ethanol. When expanded on the TLC board (a chromatographic solution of chloroform/methanol 3:1, Rf of 0.36) and sprayed with the 10% $H_2SO_4$-ethanol reagent, the compound II is purplish red.

ESI-MS m/z 531.4933[M-H]$^-$, molecular weight: 532.

Hydrogen nuclear magnetic resonance (400 MHz, $d_6$-DMSO): δ(ppm):12.0(1H, s, COOH), 7.119-7.099(1H, d, J=8.0 Hz, Ar—H), 6.530-6.943(2H, d, J=4.0 Hz, Ar—H), 6.872(3H, s, Ar—H), 6.12(2H, s), 5.39(2H, s, J=4.8 Hz), 5.23(1H, d, J=4.8 Hz), 5.1(1H, d, J=4.8 Hz), 4.800(1H, d, J=4.8 Hz), 4.374-4.388(1H, d, J=9.6 Hz), 4.105-4.085(1H, d, J=8.0 Hz), 4.005-3.982(1H, d, J=9.2 Hz), 3.75(8H, d, J=8.4 Hz), 3.422(1H, t, J=8.7 Hz), 3.08(1H, t, J=8.1 Hz), 2.85(1H, d, J=7.2 Hz);

Carbon nuclear magnetic resonance (100 MHz, $d_6$-DMSO): δ(ppm):169.75(C-17), 149.51(C-9), 148.95(C-34), 148.09(C-33), 145.74(C-8), 136.26(C-11), 131.67(C-30), 118.55(C-12), 118.05(C-13), 115.72(C-31), 112.03(C-32), 111.07(C-10), 109.92(C-35), 101.21(C-2), 100.29(C-38), 87.11(C-26), 81.74(C-22), 76.26(C-6), 75.70(C-3), 73.41(C-16), 71.91(C-4), 70.81(C-28), 69.46(C-24), 56.15(C-21), 54.47(C-29), 49.79(C-25).

According to test data of ESI-MS, 1H-NMR and 13C-NMR, the compound III is determined to have an English name of 33,34-Methylenedioxy phillygenin-8-O-β-D-glucuronide.

A structural formula of the compound III is as follows:

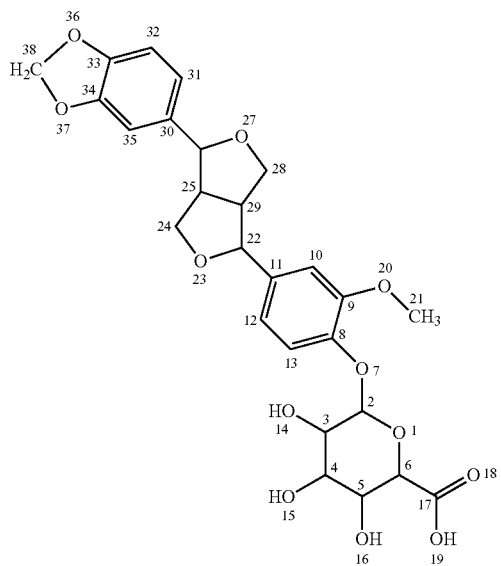 [SMILES: COc1cc(C2OCC3C(c4ccc5c(c4)OCO5)OCC23)ccc1OC1OC(C(=O)O)C(O)C(O)C1O]

Embodiment 2
1. Decocting Treatment
1-1) grinding *forsythia* leaves and enabling the *forsythia* leaves to pass through a 20-mesh sieve so as to obtain *forsythia* leaf powder, adding 9 kg of water into 1 kg of the *forsythia* leaves, uniformly mixing and heating, and performing the first decocting treatment, wherein a weight ratio of the added water to the *forsythia* leaves is 9:1; and heating and boiling, decocting and extracting for 2.5 hours, filtering so as to obtain a first extracting solution, and a first drug residue;
1-2) adding 8 kg of water into the first drug residue, heating and boiling, and performing the second decocting treatment, wherein a weight ratio of the added water to the *forsythia* leaves is 8:1; and decocting and extracting for an hour, filtering so as to obtain a second extracting solution, and a drug residue (discarding);
1-3) merging the first extracting solution and the second extracting solution so as to prepare a *forsythia* water extract;
1-4) performing vacuum concentration treatment on the *forsythia* water extract in a vacuum rotary evaporator, and recovering a solvent, thereby obtaining a *forsythia* concentrated solution (2.5 L) for later use, wherein a ratio of the weight of the *forsythia* leaves to the volume of the *forsythia* concentrated solution is 1:2.5;
2. Macroporous Resin Column Chromatography
2-1) loading the *forsythia* concentrated solution to a macroporous resin column, and performing macroporous resin column separation treatment, wherein the macroporous resin is selected from an X-5 type macroporous resin; a column volume of the macroporous resin in the macroporous resin column is 1 L (the chromatographic column has a diameter of 60 mm and a height of 500 mm, and a height of the filled resin is 354 mm); a ratio of the volume of the resin in the resin column to the weight (dry weight) of the *forsythia* leaves is 1:1 (e.g. if the dry weight of the *forsythia* leaves is 1 kg, the volume of the macroporous resin is 1 L; and if dry weight of medicinal materials is 1 g, the volume of the macroporous resin is 1 ml); washing with deionized water in an amount of 8 times the volume of the column (that is, 8 L) and removing the eluent after a concentrated supernatant completely flows into the resin column; eluting with an ethanol solution at a mass concentration of 3% in an amount of 4 times the volume of the column (that is, 4 L), and removing the eluent; and eluting with an absolute ethyl alcohol in an amount of 8 times the volume of the column (that is, 8 L), and collecting the eluent, thereby obtaining a *forsythia*-macroporous resin eluent;
2-2) performing vacuum concentration treatment on the *forsythia*-macroporous resin eluent in a rotary evaporator, recovering a solvent, drying the concentrated residue, thereby obtaining 58 g of crude *forsythia* product;
3. Performing silica-gel column chromatography
3-1) weighing 0.8 g of the crude *forsythia* product, adding a proper amount of water (1.6 ml), and stirring and dissolving for later use;
3-2) performing chromatography treatment on the crude *forsythia* product by adopting a high-performance liquid chromatograph (a Shimadzu SCL-10AVP semi-preparative high-performance liquid chromatograph, an LC-8A pump and an SPD-20A monitor), separating and purifying the crude *forsythia* product, injecting (loading) the dissolved crude *forsythia* product into the semi-preparative high-performance liquid chromatograph, and performing gradient elute by taking a methanol-water solution as an eluent, wherein a size of a chromatographic column in the high-performance liquid chromatograph is Φ22.2×250 mm, C18 reversed-phase silica-gel serves as packing, the particle size is 10 μm, the loading quantity is 800 mg, the methanol-water solution serves as a mobile phase, conditions of the gradient elute are that: gradient elute: 0-25 min, the methanol concentration is 30%-50%; gradient elute: 25-50 min, the methanol concentration is 50%-50%; the flow velocity is 4 ml/min; the column temperature is 20° C.; and an UV detection wavelength is 273 nm; and respectively collecting fractions at retention time of 25.5-27.5 min, 30.5-32.5 min and 35.5-37.5 min;
3-3) respectively performing vacuum concentration on the three collected fractions, performing vacuum drying, thereby obtaining a compound A (104.2 mg), a compound B (74.3 mg) and a compound C (58.1 mg) respectively.

The content of the compounds A, B and C is respectively detected by adopting HPLC (High Performance Liquid Chromatography), and detection conditions of the HPLC comprise: instrument: Water 515 pump; 2487 detector; chromatographic column: Kromasil RP-C18; mobile phase: acetonitrile: 0.1% phosphoric acid solution (13:87); detection wavelength: 230 nm; and flow velocity: 1.0 ml/min.

According to the HPLC detection, the purity of the compound A is 99.3%, the purity of the compound B is 98.4%, and the purity of the compound C is 98.5%.

The physicochemical properties, mass spectrums and nuclear magnetic resonance data of the compounds A, B and C prepared in the embodiment 2 are respectively the same as those of the compounds I, II and III prepared in the embodiment 1.

Test Case 1 In-Vitro Antiviral Test
1.1 Test Material
(1) Drugs
① Tested Drugs
The phillygenin glucuronide derivatives (that is, the compounds I, II and III) prepared in the embodiment 1 of the present invention.
② Positive Control Drugs
Ribavirin injection: colorless transparent liquid, produced by Henan Runhong Pharmaceutical Co., Ltd., product batch number: 1206261, SFDA approval number: H19993553, 100 mg/ml, serving as a positive control drug of the test;

Oseltamivir phosphate: provided by the National Institutes for Food and Drug Control, product batch number: 101096-200901, 100 mg/piece, serving as a positive control drug of the test;

Phillygenin: white powder, produced by Dalian Fusheng Natural Drug Development Co., Ltd., measured through high-performance liquid chromatography by two detectors such as an UV detector and an evaporative light scattering detector by virtue of an area normalization method, having purity of 99.2%.

The drugs are all dissolved in purified water, filtered, degermed to be split charged for later use at 4° C. and serve as to-be-detected drugs in the test.

(2) Cell Strains

Vero strains (African green monkey kidney cells): collected by School of Basic Medicine in Jilin University.

(3) Virus Strains

① Influenza virus strains, parainfluenza virus strains and respiratory syncytial virus (RSV) strains: purchased from Institute of Virology in Chinese Academy of Preventive Medicine; ② Coxsackie virus B3 (CVB3) strains: purchased from Wuhan Institute of Virology of Chinese Academy of Sciences; ③ Coxsackie virus A16 (CoxA16) strains, enterovirus EV71 strains: purchased from Sendai State Hospital; denovirus ④ adenovirus (AdV): purchased from Institute of Pediatrics in the First Hospital of Norman Bethune Medical University; and ⑤ hcrps simplex virus I (HSV-1): purchased from the National Institutes for Food and Drug Control.

(4) Main Equipment and Reagents

Biosafety cabinets: BHC-1300IIA/B3, AIRTECH; CO2 incubators: MCO-18AIC, SANYO; inverted microscopes: CKX41, OLYMPUS; electronic analytical balances: AR1140/C, DHAUS; culture media: DMEM, HyClone; fetal calf serum: HyClone; trypsin: Gibco; MTT: Sigma; DMSO: Tianjin Beilian Fine Chemicals Development Co., Ltd.

1.2 Test Method (1) Cell Preparation

Performing subculture on Vero cells for 1-2 days to form sheets and have clear boundaries, performing trypsin digestion when stereoscopic impression and diopter are high, completely absorbing digestive juice when needle tip shaped holes occur on cells surfaces, blowing away the cells with milliliters of culture solution, counting, diluting to the quantity of $5 \times 10^7$ cells/L with the culture solution (DMEM containing 10% fetal calf serum), inoculating in a 96-well culture plate, and enabling the cells to grow to a single layer.

(2) Drug Toxicity Determination

Cytotoxicity test: drugs are diluted with a maintenance solution (DMEM containing 2% fetal calf serum) according to concentrations shown in Table 1-1, and are used for cytotoxicity determination.

Dripping the drugs of different concentrations in Table 1-1 on single-layer Vero cells, wherein 0.2 ml of drug is filled in each well, and each concentration occupies 6 complex wells; additionally setting 6-well normal control (normal control without drugs) and 6-well blank control (culture solution), culturing in 5% $CO_2$ incubators at 37° C., observing CPE (cytopathic effect) through inverted microscopes every day (in in-vitro experiments, cell viruses are killed by cell culture and inoculation, and phenomena that the cells are rounded, die and drop from bottle walls and the like can be observed by microscopes within a certain time, called the cytopathic effect. The cytopathic effect refers to cellular degeneration caused by tissue culture cells infected by viruses. Virus quantitation can be performed by utilizing the cytopathic effect); recording the CPE; adding 20 μL (5 mg.mL$^{-1}$) of MTT (3-(4,5-dimethyl-2-thiazolyl)-2,5-diphenyl-2-H-tetrazolium bromide which has a trade name of thiazolyl blue and is a yellow dye) solution into each well within 72 hours, continuously incubating for 4 hours, sucking the culture solution in each well, adding 100 μL of DMSO into each well, oscillating for 5min, measuring an OD value at 492 nm, and calculating cell viability; performing Probit regression analysis on the cell viability in SPSS 18.0 statistical software, and calculating the maximum non-cytotoxic concentration ($TC_0$) and semi-cytotoxic concentration ($TC_{50}$).

(3) Determination of $TCID_{50}$ of Various Viruses

Performing 10-time gradient decreasing dilution on the various viruses to reach different degrees of dilution such as $10^{-1}$, $10^{-2}$, $10^{-3}$, $10^{-4}$, $10^{-5}$, and $10^{-6}$, sequentially inoculating the viruses on a single-layer Vero cell 96-well culture plate, wherein the amount of viruses in each well is 100 μL, and each degree of dilution exists in 6 wells; setting a normal cell control group, incubating in 5% $CO_2$ at 37° C. for 2 hours, removing the virus solution, adding 100 μL of cell maintenance solution into each well, and culturing in 5% $CO_2$ at 37° C.; starting to observe cytopathic effect results from the third day under the microscope, judging results on the 7-8$^{th}$ day and making a record, taking the highest degree of dilution capable of enabling 50% of cell wells to produce positive lesions as an endpoint, and calculating virus titers by using a karber method.

The formula is:

$$LogTCID_{50} = XM + \frac{1}{2}d - d\frac{\Sigma Pi}{100}$$

$TCID_{50}$: 50% tissue cell infection amount

XM: logarithm of the highest concentration dilution degree of the viruses d: logarithm of dilution degree coefficient (multiple)

TABLE 1-1

Cytotoxicity test concentrations of drugs (unit: g/L)

| Drugs | Gradient 1 | Gradient 2 | Gradient 3 | Gradient 4 | Gradient 5 | Gradient 6 | Gradient 7 | Gradient 8 |
|---|---|---|---|---|---|---|---|---|
| Compound I | 5 | 2.5 | 1.25 | 0.625 | 0.3125 | 0.15625 | 0.078125 | 0.039063 |
| Compound II | 5 | 2.5 | 1.25 | 0.625 | 0.3125 | 0.15625 | 0.078125 | 0.039063 |
| Compound III | 5 | 2.5 | 1.25 | 0.625 | 0.3125 | 0.15625 | 0.078125 | 0.039063 |
| Ribavirin | 5 | 2.5 | 1.25 | 0.625 | 0.3125 | 0.15625 | 0.078125 | 0.039063 |
| Oseltamivir phosphate | 2 | 1 | 0.5 | 0.25 | 0.125 | 0.0625 | 0.03125 | 0.015625 |
| Phillygenin | 5 | 2.5 | 1.25 | 0.625 | 0.3125 | 0.15625 | 0.078125 | 0.039063 |

Σpi: sum of lesion percentages of various degrees of dilution (4) Influences of Drugs on Virus-Iinduced CPE Taking a culture plate grown with single-layer cells, sucking and removing the culture solution, inoculating the cells by a virus attack amount corresponding to 100TCID50, adsorbing in 5% $CO_2$ incubators at 37° C. for 2 hours, adding each drug solution of a specific concentration (nearly the maximum non-cytotoxic concentration), culturing at each concentration in 6 complex wells according to the volume of 200 μL/well; setting ribavirin Injection and oseltamivir phosphate as positive drug control groups, simultaneously setting a normal control group (without any virus or drug) and a virus control group (a control group added with viruses without any drug), and observing the influences of the drugs on the virus-induced CPE; measuring an OD value under the wavelength of 492 nm by using an MTT colorimetric method, calculating antiviral effective rates (ER %) of the drugs; and comparing obvious differences among the antiviral effective rates of the various drugs in the SPSS 18.0 statistical software by using an ANOVA method.

ER %=(OD mean value of the drug treatment group–OD mean value of the virus control group)/(OD mean value of the cell control group–OD mean value of the virus control group)×100%

1.3 Test results (1) $TCID_{50}$ of Various Viruses $$\text{Parainfluenza virus: } Log TCID_{50} = -2 + 0.5 - \frac{100 + 100 + 50}{100} = -4$$

$$\text{Influenza virus: } Log TCID_{50} = -2 + 0.5 - \frac{100 + 100 + 50}{100} = -4$$

$$CVB_3: Log TCID_{50} = -2 + 0.5 - \frac{100 + 100 + 100 + 50}{100} = -5$$

$$HSV\text{-}1: Log TCID_{50} = -2 + 0.5 - \frac{100 + 100 + 100 + 30}{100} = -4.8$$

$$AdV: Log TCID_{50} = -2 + 0.5 - \frac{100 + 100 + 50}{100} = -4$$

$$RSV: Log TCID_{50} = -2 + 0.5 - \frac{100 + 100 + 100 + 50}{100} = -5$$

$$CoxA16: Log TCID_{50} = -2 + 0.5 - \frac{100 + 100 + 100 + 50}{100} = -5$$

$$EV71: Log TCID_{50} = -2 + 0.5 - \frac{100 + 100 + 100 + 50}{100} = -5$$

(2) Drug Toxicity Determination Results

1) Determination of drugs on cytotoxicity

The maximum non-cytotoxic concentration ($TC_0$) and semi-cytotoxic concentration ($TC_{50}$) of the various drugs on the Vero cells are shown in Table 1-2.

TABLE 1-2

Cytotoxicity test results of drugs (unit: g/L)

| Concentration | Compound I | Compound II | Compound III | Ribavirin | Oseltamivir phosphate | Phillygenin |
|---|---|---|---|---|---|---|
| Maximum non-cytotoxic concentration | 0.106 | 0.103 | 0.0906 | 0.063 | 0.27 | 0.012 |
| Semi-cytotoxic concentration | 0.482 | 0.412 | 0.435 | 1.382 | 0.834 | 0.293 |

2) Protective Effect Results of Drugs on Virus-Induced CPE

See effective rates of drugs on various viruses and one-way ANOVA (Analysis of Variance) results in Table 1-3 in detail.

TABLE 1-3

Statistical table for antiviral effective rates (ER %) of drugs

| Drug Virus | Compound I | Compound II | Compound III | Ribavirin | Oseltamivir phosphate | Phillygenin |
|---|---|---|---|---|---|---|
| Influenza virus | 95.81** | 92.74** | 91.35** | 56.44** | 82.19** | 88.17** |
| Parainfluenza virus | 96.24** | 90.13** | 92.22** | 95.13** | 92.11** | 94.06** |
| CoxA16 | 100.00** | 99.25** | 100.00** | 0.72 | 2.94 | 97.03** |
| RSV | 83.21** | 81.14** | 86.18** | 52.15* | 39.22 | 81.41** |
| HSV-I | 91.23** | 93.35** | 96.06** | 64.65** | 63.24** | 85.36** |
| ADV | 21.26* | 20.46* | 22.17* | 0.47 | 12.12 | 14.25* |
| EV71 | 52.15 | 54.32 | 51.64 | 4.03** | 48.65 | 32.27 |
| CVB3 | 10.16 | 11.18 | 9.63 | 12.14 | 1.53 | 2.29 |

Notes:
compared with the virus control group, *P < 0.05, **P < 0.01; and compared with the phillygenin,
P < 0.05, ##P < 0.01.

The results in the Table 1-3 show that 33-Hydroxy phillygenin-8-O-β-D-glucuronide (compound I), 9-Hydroxy phillygenin-8-O-β-D-glucuronide (compound II) and 33,34-Methylenedioxy phillygenin-8-O-β-D-glucuronide (compound III) have inhibition rates and effective rates exceeding 90% on the influenza virus, the parainfluenza virus, the herpes simplex virus I (HSV-I) and enterovirus EV71, have obvious differences from the virus control group and have statistical significances. The 33-Hydroxy phillygenin-8-O-β-D-glucuronide, 9-Hydroxy phillygenin-8-O-β-D-glucuronide and 33,34-Methylenedioxy phillygenin-8-O-β-D-glucuronide have antiviral curative effects on multiple viruses superior to the advantages of the phillygenin, Ribavirin and Oseltamivir phosphate.

Test Case 2 In-Vivo Antiviral Test 2.1 Test Material (1) Laboratory Animals

Kunming mice: weight of 18-22 g, half male and half female, purchased from Laboratory Animal Center in Dalian Medical University, quality certificate number: SCXK (13) 2012-0003.

(2) Drugs

① The compound I prepared in the embodiment 1 of the present invention, that is, 33-Hydroxy phillygenin-8-Oβ-D-glucuronide;

② Ribavirin injection: colorless transparent liquid, produced by Henan Runhong Pharmaceutical Co., Ltd., product batch number: 1206261, SFDA approval number: H19993553, 100 mg/ml, serving as a positive control drug of the test;

③ Oseltamivir phosphate: provided by the National Institutes for Food and Drug Control, product batch number: 101096-200901, 100 mg/piece, serving as a positive control drug of the test;

④ Phillygenin: white powder, produced by Dalian Fusheng Natural Drug Development Co., Ltd., measured through high performance liquid chromatography by two detectors (such as an UV detector and an evaporative light scattering detector) by virtue of an area normalization method, having purity of 99.2%.

The drugs are all dissolved in purified water, filtered, degermed to be split charged for later use at 4° C. and serve as to-be-detected drugs in the test.

(2) Detecting Instruments and Reagents

| Instrument Name | Model | Manufacturer |
| --- | --- | --- |
| Quantitative PCR insturment | 7300 | ABI |
| PCR instrument | ES-60J | Shenyang Longteng Electronic Weighing Instrument Co., Ltd. |
| Electronic analytical balance | FA1004 | Shenyang Longteng Co., Ltd. |
| CO$_2$ incubator | HG303-5 | Nanjing Experimental Instrument Plant |
| Clean bench | SW-CJ-IF | Suzhou Antai Technology Co., Ltd. |
| Inverted microscope | CKX41 | Olympus Instrument Australia |
| −80° C. ultralow temperature refrigerator | TECON-5082 | |
| Water bath oscillator | HZS-H | Harbin Donglian Co., Ltd. |
| ELIASA | TECAN A-5082 | Australia |
| Spectrophotometer | 7550 type | Japan |

2.2 Test Method (1) Determination of influenza virus and parainfluenza virus on half lethal dose of mice Performing 10-time gradient dilution on the influenza virus and parainfluenza virus (cell lysis buffer) to obtain virus solutions with concentrations of $10^{-1}$, $10^{-2}$, $10^{-3}$, $10^{-4}$ and $10^{-5}$; taking 120 Kunming mice, 60 influenza viruses and 60 parainfluenza viruses, respectively randomly dividing into 6 groups, lightly anesthetizing the mice with ethyl ether, performing nasal inhalation to infect the virus solutions of different degrees of dilution at a dose of 0.03 mL per mouse; simultaneously setting blank control, replacing virus suspension with normal saline, taking death and survival as observation indexes, observing the mice every day within 14 days after infection, not counting mice suffering from nonspecific death within 24 hours after infection, and calculating LD50 of the virus solution by a Karber method, wherein the calculation formula is: Log $LD_{50}$=XM+1/2 d−dΣPi/100 [wherein: $TCID_{50}$: the half lethal dose; XM: logarithm of the highest concentration dilution degree of the viruses; d: logarithm of dilution degree coefficient (multiple); Σpi: sum of lesion percentages of various degrees of dilution].

(2) Study of 33-Hydroxy phillygenin-8-O-β-D-glucuronide for resisting pneumonia caused by infection of influenza virus and parainfluenza virus 1) Laboratory Animals and Groups taking 960 Kunming mice at an age of four weeks for carrying out two tests; taking 480 mice, randomly dividing the mice into 48 groups at a quantity of 10 mice in one group to be used for test of determining the 33-Hydroxy phillygenin-8-O-β-D-glucuronide on lung indexes and lung index inhibition rates of the mice infected by the influenza virus, and repeatedly testing for 3 times, wherein 80 mice are taken each time; taking the other 480 mice, randomly dividing the mice into 48 groups at a quantity of 10 mice in one group to be used for test of determining the 33-Hydroxy phillygenin-8-O-β-D-glucuronide on lung suspension virus hemagglutination titers, and repeatedly testing for 3 times, wherein 80 mice are taken each time.

2) Infection Method

Putting a ball of degreasing cotton into a 200-300 mL of beaker, pouring a proper amount of ethyl ether (just enabling the degreasing cotton to be wetted), backing off the beaker filled with the degreasing cotton, putting a mouse for anesthetizing, then the mouse is extremely excited, turning up the mouse when the mouse is obviously weak, performing nasal inhalation to infect the influenza virus and parainfluenza virus at a dose of 0.03 ml per naris, and replacing the virus suspension with the normal saline in the normal control group.

3) Administration Method and Administration Dosage

Respectively performing regular intragastric administration on 33-Hydroxy phillygenin-8-O-β-D-glucuronide groups, ribavirin control groups and oseltamivir phosphate control groups within one day before infection, wherein high, medium and low administration dosages of the 33-Hydroxy phillygenin-8-O-β-D-glucuronide are respectively 10.0 mg/kg, 5.0 mg/kg and 2.5 mg/kg, an administration dosage of the positive drug ribavirin is 58.5 mg/kg, an administration dosage of the positive drug oseltamivir phosphate is 19.5 mg/kg, and an administration dosage of the phillygenin is 13.0 mg/kg; continuously administrating once a day for 5 days, and performing intragastric administration with the normal saline of the same volume in the virus control groups.

4) Observation Indexes

① Lung Index Determination

Inhibiting from food and water for 8 hours on the fifth day after administration of each mouse, weighing, extracting eyeballs, bloodletting, killing the animals, opening the chest to extract the total lung, washing the lung with the normal saline twice, sucking the surface moisture dry by using filter paper, weighing the lung by using an electronic balance, and calculating the lung index and the lung index inhibition rate according to the following formula:

lung index=(mouse lung weight/mouse body weight)×100%; lung index inhibition rate= (mean lung index of the infection model group-mean lung index of the test group)/mean lung index of the infection model group×100%.

② Lung Suspension Virus Hemagglutination Titer Determination

Respectively taking lungs of mice in various groups on the fifth day after treatment, grinding the lungs into homogenate by a homogenizer at a low temperature, diluting the homogenate into 10% of lung tissue suspension with the normal saline, centrifuging to take the supernatant, performing doubling dilution, dripping onto a titer plate according to 0.2 ml/well, adding 0.2 ml of 1% chicken erythrocyte suspension into each well, uniformly mixing, standing at a room temperature for 30 minutes, and observing and recording the hemagglutination titer, wherein erythrocyte agglutination (++) time is taken as the endpoint, and the suspension dilution ratio represents the titer.

2.3 Test Results and Analysis (1) Determination Results of Influenza Virus and Parainfluenza Virus on Half Lethal Dose of Mice The Kunming mice in the test groups are respectively subjected to nasal inhalation to be infected with 30 μL of influenza virus and parainfluenza virus of different concentrations, on the third day after infection, the mice in the previous 3 groups (groups with respective virus concentrations of $10^{-1}$, $10^{-2}$ and $10^{-3}$) have disease symptoms of different degrees as follows: pilomotor fur, shiver, decreased appetite and the like; on the fifth day, the mice wobble; on the sixth day, mice in the group with the highest virus concentration start to die, and mice in the other various groups start to die in succession from the seventh day after infection. After 14-day observation is finished, the numbers of dead mice in the various groups are counted, and results are shown in the following Table 1-4 and Table 1-5. The $LD_{50}$ of the influenza virus is calculated to be the dilution of $10^{-2.5}$, and the $LD_{50}$ of the parainfluenza virus is calculated to be the dilution of $10^{-2.5}$.

TABLE 1-4

Statistics of test results of influenza virus on half lethal dose

| Influenza virus group | Cumulative death | Cumulative survival | Cumulative death rate |
|---|---|---|---|
| $10^{-1}$ Group | 9 | 1 | 90% |
| $10^{-2}$ Group | 7 | 3 | 70% |
| $10^{-3}$ Group | 4 | 6 | 40% |
| $10^{-4}$ Group | 3 | 7 | 30% |
| $10^{-5}$ Group | 1 | 9 | 10% |
| Blank Group | 0 | 10 | 0% |

$LD_{50}$ of viruses is calculated by the Karber method. $LogLD_{50}$ of the influenza virus is as follows:

$$LogLD_{50} = XM + \frac{1}{2}d - d\frac{\Sigma Pi}{100} =$$
$-1 + 0.5 - (80\% + 60\% + 40\% + 20\% + 0\% + 0\%) = -2.9$

TABLE 1-5

Statistics of test results of parainfluenza virus on half lethal dose

| Parainfluenza virus group | Cumulative death | Cumulative survival | Cumulative death rate |
|---|---|---|---|
| $10^{-1}$ Group | 8 | 2 | 80% |
| $10^{-2}$ Group | 6 | 4 | 60% |
| $10^{-3}$ Group | 4 | 6 | 40% |
| $10^{-4}$ Group | 2 | 8 | 20% |
| $10^{-5}$ Group | 0 | 10 | 0% |
| Blank Group | 0 | 10 | 0% |

$LD_{50}$ of viruses is calculated by the Karber method. $LogLD_{50}$ of the parainfluenza virus is as follows:

$$LogLD_{50} = XM + \frac{1}{2}d - d\frac{\Sigma Pi}{100} =$$
$-1 + 0.5 - (90\% + 70\% + 40\% + 30\% + 10\% + 0\%) = -2.5$ (2) Action Results of 33-Hydroxy phillygenin-8-O-β-D-glucuronide for Resisting Pneumonia Caused by Infection of Influenza Virus and Parainfluenza Virus ① Lung Index Determination After the mice are infected by the influenza virus and the parainfluenza virus, the determination results of the mean lung index show that: compared with the infection model group, the concentrations of the 33-Hydroxy phillygenin-8-O-β-D-glucuronide have a certain protective effects in a range of 2.25-10.0 mg/kg/d, and the lung indexes are obviously decreased; curative effects of high-dose 33-Hydroxy phillygenin-8-O-β-D-glucuronide groups on the influenza virus and the parainfluenza virus are superior to the curative effects of the phillygenin group (P<0.05).

Test results are shown in Table 1-6 and Table 1-7.

TABLE 1-6

Influences of compound I on lung indexes and lung index inhibition rates of mice infected with influenza virus (n = 3)

| Group | | Drug dose (mg/kg/d) | Lung index ($\bar{X}$± S) | Lung index inhibition rate (%) | P value |
|---|---|---|---|---|---|
| Normal control group | | 0 | 1.273 ± 0.101 | — | |
| Virus control group | | 0 | 1.475 ± 0.026 | — | |
| Ribavirin group | | 58.5 | 1.279 ± 0.056 | 13.84 | *<0.05 |
| Oseltamivir phosphate group | | 19.5 | 1.176 ± 0.045 | 19.76 | *<0.01 |
| Phillygenin group | | 13.0 | 1.208 ± 0.025 | 11.67 | *<0.05 |
| Compound I | High-dose group | 10.0 | 1.145 ± 0.037 | 22.82 | **<0.01, #<0.05 |
| | Medium-dose group | 5.0 | 1.187 ± 0.028 | 20.03 | **<0.01, #<0.05 |

TABLE 1-6-continued

Influences of compound I on lung indexes and lung index inhibition rates of mice infected with influenza virus (n = 3)

| Group | Drug dose (mg/kg/d) | Lung index ($\overline{X} \pm S$) | Lung index inhibition rate (%) | P value |
|---|---|---|---|---|
| Low-dose group | 2.25 | 1.225 ± 0.034 | 17.85 | *<0.05, >0.05 |

Compared with the virus control group, *P < 0.05, **P < 0.01; and compared with the phillygenin group, #P < 0.05, ##P < 0.01.

TABLE 1-7

Influences of compound I on lung indexes and lung index inhibition rates of mice infected with parainfluenza virus (n = 3)

| Group | | Drug dose (mg/kg/d) | Lung index ($\overline{X} \pm S$) | Lung index inhibition rate (%) | P value |
|---|---|---|---|---|---|
| Normal control group | | 0 | 1.303 ± 0.037 | — | |
| Virus control group | | 0 | 1.585 ± 0.056 | — | |
| Ribavirin group | | 58.5 | 1.337 ± 0.056 | 15.68 | *<0.01 |
| Oseltamivir phosphate group | | 19.5 | 1.241 ± 0.046 | 21.83 | *<0.01 |
| Phillygenin group | | 13.0 | 1.349 ± 0.046 | 14.56 | *<0.01 |
| Compound I | High-dose group | 13.0 | 1.239 ± 0.037 | 22.26 | *<0.01, #<0.05 |
| | Medium-dose group | 6.5 | 1.277 ± 0.054 | 19.73 | *<0.01, #<0.05 |
| | Low-dose group | 3.25 | 1.318 ± 0.028 | 16.94 | *<0.01, >0.05 |

Compared with the virus control group, *P < 0.05, **P < 0.01; and compared with the phillygenin group, #P < 0.05, ##P < 0.01.

② Lung Suspension Virus Hemagglutination Titer Determination

After the mice are infected by the influenza virus and the parainfluenza virus, lung tissue virus hemagglutination titers (InX) in the infection model groups are respectively 31.64 and 32.06; after the mice are treated with the 33-Hydroxy phillygenin-8-O-β-D-glucuronide of different concentrations by 5 days, the lung tissue virus hemagglutination titers are slightly decreased; compared with the infection model group, differences are obvious (P<0.01), wherein the virus hemagglutination titers on the influenza virus and the parainfluenza virus in the medium—and high-dose 33-Hydroxy phillygenin-8-O-β-D-glucuronide groups are obviously lower than that in the model group, the inhibition rates are all higher than the inhibition rate in the phillygenin group, and differences are obvious (P<0.05, p<0.01). Test results are shown in Table 1-8 and Table 1-9.

TABLE 1-8

Influences of compound I on lung suspension hemagglutination titers of mice infected with influenza virus (n = 3)

| Group | | Drug dose (mg/kg/d) | Hemagglutination titer (InX) | Inhibition rate (%) | P value |
|---|---|---|---|---|---|
| Normal control group | | 0 | 0 | | |
| Virus control group | | 0 | 32.06 ± 1.095 | | |
| Ribavirin group | | 58.5 | 21.87 ± 1.050 | 32.35 | **<0.01 |
| Oseltamivir phosphate group | | 19.5 | 20.47 ± 1.104 | 35.26 | **<0.01 |
| Phillygenin group | | 13.0 | 21.15 ± 1.024 | 29.15 | *<0.01 |
| Compound I | High-dose group | 10.0 | 19.24 ± 0.513 | 40.28 | **<0.01, ##<0.01 |
| | Medium-dose group | 5.0 | 20.37 ± 0.285 | 36.32 | **<0.01, #<0.05 |
| | Low-dose group | 2.25 | 22.16 ± 1.270 | 31.26 | **<0.01, >0.05 |

Compared with the virus control group, *P < 0.05, **P < 0.01; and compared with the phillygenin group, #P < 0.05, ##P < 0.01.

TABLE 1-9

Influences of compound I on lung suspension hemagglutination titers of mice infected with parainfluenza virus (n = 3)

| Group | | Drug dose (mg/kg/d) | Hemagglutination titer (lnX) | Inhibition rate (%) | P value |
|---|---|---|---|---|---|
| Normal control group | | 0 | 0 | | |
| Virus control group | | 0 | 33.17 ± 1.190 | | |
| Ribavirin group | | 58.5 | 24.32 ± 1.123 | 23.25 | *<0.01 |
| Oseltamivir phosphate group | | 19.5 | 23.24 ± 1.242 | 31.14 | *<0.01 |
| Phillygenin group | | 13.0 | 23.63 ± 1.156 | 27.75 | *<0.01 |
| Compound I | High-dose group | 10.0 | 19.68 ± 0.638 | 38.36 | *<0.01, #<0.01 |
| | Medium-dose group | 5.0 | 20.47 ± 0.583 | 36.32 | *<0.01, #<0.05 |
| | Low-dose group | 2.25 | 21.62 ± 0.553 | 33.61 | *<0.01, |

Compared with the virus control group, *P < 0.05, **P < 0.01; and compared with the phillygenin group, #P < 0.05, ##P < 0.01.

2.4 Conclusion

In-vivo antiviral test results show that the 33-Hydroxy phillygenin-8-O-β-D-glucuronide has obvious inhibitory effects on the influenza virus and the parainfluenza virus as well as mouse virus pneumonia caused by the viruses in the dosage range of 2.25-10 mg/kg/d and can achieve effects of obviously decreasing the lung indexes and hemagglutination titers of the mice and obviously improving pulmonary pathology, and compared with the virus model control group, the differences are obvious; and moreover, the curative effects of the medium-and high-dose 33-Hydroxy phillygenin-8-O-β-D-glucuronide groups are obviously superior to that of the phillygenin (*P<0.05 or **P<0.01), and the medium-and high-dose group have a trend of being superior to the ribavirin and oseltamivir phosphate.

The compounds II and III are the same as the compound I, have obvious inhibitory effects on the influenza virus and the parainfluenza virus as well as the mouse virus pneumonia caused by the viruses, and can achieve effects of obviously decreasing the lung indexes and hemagglutination titers of the mice and obviously improving the pulmonary pathology, and compared with the virus model control group, the differences are obvious.

The invention claimed is:

1. A preparation method of a phillygenin glucuronic acid derivative, the method sequentially comprises the following steps:

1) mixing forsythia leaves and extraction solvent water and heating, decocting and extracting for 2-3 times, and collecting and merging the extracting solution, and thereby obtaining a forsythia water extract;

2) separating the forsythia water extract by adopting a macroporous resin column, and collecting and merging the eluent, and thereby obtaining a forsythia resin column eluent;

3) performing silica-gel column chromatography on the forsythia resin column eluent, collecting the eluent at stages, respectively drying the eluent, thereby obtaining the phillygenin glucuronic acid derivative, and the phillygenin glucuronic acid derivative comprises a general molecular formula shown as a formula (I):

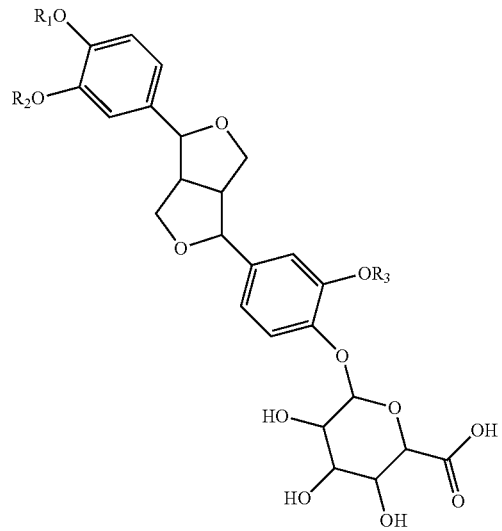

wherein, $R_1$=H, $R_2$=$C_nH_{2n+1}$, $R_3$=$C_nH_{2n+1}$ or $R_1$=$C_nH_{2n+1}$, $R_2$=$C_nH_{2n+1}$, $R_3$=H or $R_1$-$R_2$=—$CH_2$—, $R_3$=$C_nH_{2n+1}$; n=1.

2. The preparation method of claim 1, wherein in each decocting process in the step 1), a weight ratio of the forsythia leaves to the extraction solvent water is 1:6-10.

3. The preparation method of claim 1, wherein the method further comprises the following steps: concentrating the forsythia water extract in the step 1), preparing a forsythia concentrated solution, and performing macroporous resin column separation treatment.

4. The preparation method of claim 3, wherein a ratio of the volume of the forsythia concentrated solution prepared by concentration treatment to the weight of the forsythia leaves is a range from 1:1 to 5:1.

5. The preparation method of claim 1, wherein in the step 3), C18 reversed-phase silica-gel serves as packing in the silica-gel column chromatography process; specifications of a chromatographic column comprise an internal diameter of 10-100 mm and a length of 10-300 mm; a particle size of the packing is 5-10 μm; and a mobile phase is eluted in an isocratic elution manner or a gradient elution manner.

6. The preparation method of claim 5, wherein the mobile phase in the silica-gel column chromatography process is a mixed solution of methanol and water, wherein a volume ratio of the methanol to the water is 8:2-10:1.

7. A method of treating a human patient in need of treatment for influenza virus infection, wherein the method comprises administering to the patient a phillygenin glucuronic acid derivative, and the phillygenin glucuronic acid derivative comprises a general molecular formula shown as a formula (I):

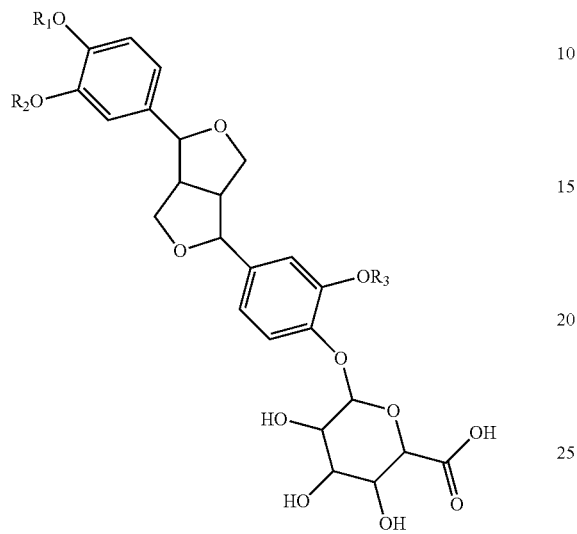

wherein, $R_1=C_nH_{2n+1}$, $R_2=C_nH_{2n+1}$, $R_3H$ or $R_1\text{-}R_2=CH_2\text{---}$, $R_3=C_nH_{2n+1}$; n=1-30.

* * * * *

UNITED STATES PATENT AND TRADEMARK OFFICE
CERTIFICATE OF CORRECTION

| | |
|---|---|
| PATENT NO. | : 10,407,455 B2 |
| APPLICATION NO. | : 15/565249 |
| DATED | : September 10, 2019 |
| INVENTOR(S) | : Li Fu |

It is certified that error appears in the above-identified patent and that said Letters Patent is hereby corrected as shown below:

In the Specification

Column 13, Line 27, delete "hcrps" and insert --herpes--.

Column 18, Line 3, after the word "mice", begin a new paragraph.

Page 1 of 1

Signed and Sealed this
Seventh Day of July, 2020

Andrei Iancu
*Director of the United States Patent and Trademark Office*